US006503892B2

(12) United States Patent
Schuman et al.

(10) Patent No.: US 6,503,892 B2
(45) Date of Patent: Jan. 7, 2003

(54) METHOD OF USING MATRIX METALLOPROTEINASE INHIBITORS IN FILTERING BLEBS FOLLOWING GLAUCOMA FILTERING SURGERY AND IN THE TREATMENT OF ISCHEMIC DAMAGE TO THE RETINA AND OPTIC NERVE

(75) Inventors: Joel S. Schuman, Wayland, MA (US); M. Elizabeth Fini, Milton, MA (US); Shravan K. Chintala, Quincy, MA (US)

(73) Assignee: New England Medical Center Hospitals Inc., Boston, MA (US)

( * ) Notice: Subject to any disclaimer, the term of this patent is extended or adjusted under 35 U.S.C. 154(b) by 0 days.

(21) Appl. No.: 09/841,936

(22) Filed: Apr. 25, 2001

(65) Prior Publication Data

US 2002/0042402 A1 Apr. 11, 2002

Related U.S. Application Data

(60) Provisional application No. 60/199,881, filed on Apr. 26, 2000.

(51) Int. Cl.[7] .............................................. A01N 37/18
(52) U.S. Cl. ...................................... 514/152; 514/912
(58) Field of Search .................................. 514/152, 912

(56) References Cited

U.S. PATENT DOCUMENTS 5,773,430 A 6/1998 Simon et al. ................ 514/152

OTHER PUBLICATIONS

Allingham, R. Rand, "Filtering Surgery in the Management of Glaucoma," Chandler and Grant's Glaucoma, 4th Ed., 1997; 516–37.
Asahi et al., "Role of Matrix Metalloproteinase 9 after Focal Cerebral Ischemia: Effects of Gene Knockout And Enzyme Inhibition with BB–94," Journal of Cerebral Blood Flow and Metabolism, 2000; 20:1681–89.
Awan, K. J., Spaeth, P. G., "Use of Isobutyl–2–Cyanoacrylate Tissue Adhesive in the Repair of Conjunctival Fistula in Filtering Procedures for Glaucoma," Annals of Ophthalmology, 1974; 6:851–53.
Brown, P. D., "Matrix Metalloproteinase Inhibitors: A Novel Class of Anticancer Agents," Advances in Enzyme Regulation, 1995; 35:293–01.
Chen, Z. L., Strickland, S., "Neuronal Death in the Hippocampus is Promoted by Plasmin–Catalyzed Degradation of Laminin," Cell, 1997; 91:917–25.
Cordeiro et al., "Human Anti–Transforming Growth Factor –Beta 2 Antibody: A New Glaucoma Anti–Scarring Agent," Investigative Ophthalmology and Visual Science, 1999; 40:2225–34.
Crowston et al., "Antimetabolite–Induced Apoptosis in Tenon's Capsule Fibroblasts," Investigative Ophthalmology and Visual Science,1998; 39:449–54.

Dunnington, J. H., Regan, E. F., "Late Fistulization of Operative Wounds. Diagnosis and Treatment," Archives of Ophthalmology, 1950; 43:407–18.
Gehring, J. R., Ciccarelli, E. C., "Trichloroacetic Acid Treatment of Filtering Blebs Following Cataract Extraction," American Journal of Ophthalmology, 1972; 74:622–24.
Greenfield et al., "Bleb–Related Ocular Infection," Journal of Glaucoma, 1998; 7:132–36.
Greenfield et al., "Late–Onset Bleb Leaks after Glaucoma Filtering Surgery," Archives of Ophthalmology, 1998; 116:443–47.
Hennis H. L., Stewart W. C., "Use of the Argon Laser to Close Filtering Bleb Leaks," Graefe's Archive for Clinical and Experimental Ophthalmology, 1992; 230:537–41.
Joiner et al., "A Modification of the Use of the Glaucoma Tamponade Shell," Ophthalmic Surgery, 1989; 20:441–42.
Melamed et al., "Donor Scleral Graft Patching for Persistant Filtration Bleb Leak," Ophthalmmic Surgery, 1991; 22:164–65.
Morris, D. A., et al., "Use of Autologous Tenon's Capsule and Scleral Patch Grafts for Repair of Excessively Draining Fistulas with Leaking Filtering Blebs," Journal of Glaucoma, 1998; 7:417–19.
"O'Connor et al., A Surgical Method to Repair Leaking Filtering Blebs," Ophthalmic Surgery, 1992; 23:336–38.
Parrish, R., Minckler, D., ""Late Endophthalmitis"—Filtering Surgery Time Bomb?" The Journal of the American Academy of Ophthalmology, 1996; 103:1167–68.
Ritch, R. et al., "Management of the Leaking Filtration Bleb," Journal of Glaucoma, 1993; 2:114–18.
Romanic A. M. et al., "Matrix Metalloproteinase Expression Increases after Cerebral Focal Ischemia In Rats. Inhibition of Metalloproteinase–9 Reduces Infarct Size.," Stroke, 1998; 29:1020–30.
Rubinfeld et al., "Serious Complications of Topical Mitomycin–C after Pterygium–Surgery," The Journal of the American Academy of Ophthalmology, 1992; 99:1647–54.
Stamper et al., "Hypotonous Maculopathy after Trabeculectomy with Subconjunctival 5–Flourouracil," American Journal of Ophthalmology, 1992; 114:544–53.
Weber, P. A., Baker, N. D., "The Use of Cyanoacrylate Adhesive with a Collagen Shield in Leaking Filtering Blebs," Ophthalmic Surgery, 1989; 20:284–85.

(List continued on next page.)

Primary Examiner—Zohreh Fay
(74) Attorney, Agent, or Firm—Barry J. Marenberg; Ivor R. Elrifi; Mintz, Levin, Cohn, Ferris, Glovsky and Popeo, P.C.

(57) ABSTRACT

This invention provides a method of inhibiting, preventing, and/or treating conjunctival filtering bleb leaks that may occur following glaucoma filtering surgery by administering Matrix Metalloproteinase inhibitors to glaucoma patients who have undergone such surgery. The invention additionally includes a method of using Matrix Metalloproteinase inhibitors to inhibit, prevent, and/or treat ischemic damage to the retina and optic nerve in patients in need of such treatment.

42 Claims, 8 Drawing Sheets

OTHER PUBLICATIONS

Westermark, J., Kähäri V. M., "Regulation of Matrix Metalloproteinase Expression in Tumor Invasion," The FASEB Journal, 1999; 13:781–92.

Wilensky, J. T., "Management of Late Bleb Leaks Following Glaucoma Filtering Surgery," Transactions of the American Ophthalmological Society, 1992; 90:161–70.

Wilson, M. R., Kotas–Neumann, R., "Free Conjuctival Patch for Repair of Persistent Late Bleb Leak," American Journal of Ophthalmology, 1994; 117:569–74.

Wise, J. B., "Treatment of Chronic Postfiltration Hypotony by Intrableb Injection of Autologous Blood," Archives of Ophthalmology, 1993; 111:827–30.

Wojtowicz–Praga et al., "Matrix Metalloproteinase Inhibitors," Investigational New Drugs, 1997; 15:61–75.

Brown, P. D., "Synthetic Matrix Metalloproteinase Inhibitors: From Cancel Models to Cancer Patients," Proc. Ann. Meet Am. Assoc. Cancer Research, 1996; 37:633–34.

METHOD OF USING MATRIX METALLOPROTEINASE INHIBITORS IN FILTERING BLEBS FOLLOWING GLAUCOMA FILTERING SURGERY AND IN THE TREATMENT OF ISCHEMIC DAMAGE TO THE RETINA AND OPTIC NERVE

RELATED APPLICATION

The present application claims the benefit, under 35 U.S.C. §120, of U.S. Provisional Patent Application Ser. No. 60/199,881, which was filed on Apr. 26, 2000.

FIELD OF THE INVENTION

The invention relates to methods of using matrix metalloproteinase inhibitors in glaucoma filtering surgery and in the treatment of ischemic damage to the retina and optic nerve.

BACKGROUND OF THE INVENTION

The retina is comprised of a network of light sensitive nerve cells that line the back of the eye. Located at the innermost cell layer are the ganglion cells. Long filamentous extensions from the axons of these cells wind their way across the retinal surface to a central location at the back of the eye, where they turn and bunch together to form the optic nerve leading to the brain. Light-induced signals are transmitted to produce our perception of sight. The place where the axons turn is called the optic nerve head. The term glaucoma describes a group of diseases that involve optic nerve damage at the level of the optic nerve head. Glaucoma results in a progressive loss of sight and may eventually lead to blindness.

Elevated intraocular pressure (IOP) is the major risk for patients who suffer from glaucoma. In a normal subject's eye, a fluid, known as the aqueous humor, circulates freely through the anterior chamber of the eye. This fluid, which is continuously produced by the eye's ciliary body, is drained from the eye, through the trabecular meshwork, back into the bloodstream. When the fluid drains properly, an appropriate fluid pressure is maintained in the anterior chamber, maintaining the shape of the cornea. Elevated IOP develops when the filtration mechanism of the trabecular meshwork is no longer adequate, leading to an increase in fluid within the anterior chamber. This increase in fluid, in turn, leads to an increase in the IOP. It is this increase in IOP that subsequently causes pressure on the optic nerve at the level of the optic nerve head. This causes damage to the optic nerve, which, in turn, may lead to blindness.

Ischemia is defined as an arrest of blood flow and reduction of oxygen supply to a tissue or organ. Ischemic damage to the retina is a common pathological factor in a number of diseases which cause blindness in humans, including central retinal artery and vein occlusions, diabetes, retinopathy of prematurity, and glaucoma, among others. Occlusion or damage to vessels that supply blood and oxygen to the retina results in ganglion cell death and irreversible blindness.

Management of glaucoma is directed at the control of IOP. However, therapy that prevents damage at the optic nerve head and the death of ganglion cells would constitute a more direct treatment. Present information supports the working hypothesis that ganglion cell death in glaucoma may result from a particular form of ischemia. Support for this view comes from the observation that ischemia induced by occlusion of the retinal artery due to acute elevation of IOP in animals produces damage at the optic nerve head similar to that seen in glaucoma.

Presently, glaucoma is not curable by any available treatment method. However, a variety of different treatment options are available to control, and, perhaps, to slow, the progression of the disease. The choice of a particular treatment is often dependent upon the degree of progression of the disease. Possible treatment options include medicinal therapy, laser eye surgery, and/or conventional surgical methods. Although many different surgical techniques have been employed in the past, glaucoma filtering surgery, also known as trabeculectomy, is principally performed today for the surgical (i.e., non-laser) management of glaucoma. Glaucoma filtration surgery, also known as glaucoma filtering surgery ("GFS") is typically, but not necessarily, performed on patients in whom prior medicinal and laser therapies have failed to reduce the IOP to sufficiently lower levels.

Generally, GFS is performed to control the IOP when medical therapy or other measures fail. Filtration surgery lowers the IOP by creating a fistula between the anterior chamber and the subconjunctival space, creating a filtering bleb. The aqueous humor that percolates through the bleb can then either be absorbed through veins or conjunctival lymphatics or, in some cases where the conjunctiva is thin, pass directly into the tear film. The major determinant of glaucoma filtering surgery success is the conjunctival wound healing response, with excessive post-operative scarring leading to filtration failure. Late bleb leaks may compromise the ability of the bleb to regulate IOP, and can lead to bleb-related complications, such as infection and hypotony. Current modalities to treat bleb leaks include the use of aqueous suppressants (Pederson,. Ocular hypotony. St. Louis: Mosby; 1989), use of soft bandage contact lenses, pressure patching, glaucoma tamponade shell (Joiner et al., A modification of the use of the glaucoma tamponade shell, OPHTHAL SURG 1989;20:441–2), application of trichloroacetic acid (Gehring et al., Trichloroacetic acid treatment of filtering blebs following cataract extraction, AM J OPHTHALMOL 1972;74:622–4), cyanoacrylate glue (Awan et al., Use of isobutyl-2-cyanoacrylate tissue adhesive in the repair of conjunctival fistula in filtering procedures for glaucoma, ANN OPHTHALMOL 1974;6:851–3; Weber et al., The use of-cyanoacrylate adhesive with a collagen shield in leaking filtering blebs, OPHTHAL SURG 1989; 20:284–5), autologous blood injection (Wise, Treatment of chronic postfiltration hypotony by-intrableb injection of autologous blood, ARCH OPHTHALMOL 1993; 11:827–30.), application of argon laser (Hennis HL, Stewart WC. Use of the argon laser to close filtering bleb leaks, GRAEFES ARCH CLIN EXP OPHTHALMOL 1992;230:537–41), and suturing of the blebs. A variety of surgical procedures have also been used to repair leaking late-onset blebs, including conjunctival patch grafts (Wilson et al., Free conjunctival patch for repair of persistent late bleb leak, AM J OPHTHALMOL 1994; 117:569–74.), and scleral patch grafts in association with conjunctival advancement (Melamed et al., Donor scleral graft patching for persistent filtration bleb leak, OPHTHAL SURG 1991;22:164–5; Morris et al., Use of autologous Tenon's capsule and scleral patch grafts for repair of excessively draining fistulas with leaking filtering blebs, J GLAUCOMA 1998;7:417–9; O'Connor et al., A surgical method to repair leaking filtering blebs, OPHTHAL SURG 1992;23:336–8; Dunnington, Late fistulization of operative wounds. Diagnosis and treatment, ARCH.OPHTHALMOL.1950;43:407–418). Successful closure of late-onset bleb leaks often requires surgical revision of the bleb (Ritch et al., Cases in controversy: Management of the leaking filtration bleb, J GLAUCOMA 1993;2:114–118).

The filtration surgery technique is designed to provide an alternative pathway for the aqueous humor fluid to leave the eye. More specifically, during filtration surgery the filtering or conjunctival bleb is created which serves as an auxiliary "drain" on the outside of the eyeball, and which has direct communication to the inside of the eyeball. This alternate pathway has a lower resistance to fluid outflow than that of the failing, or irreversibly obstructed, trabecular meshwork found in the glaucoma patient. The desired result of this technique is to achieve a lower IOP that is compatible with normal optic nerve function.

Because the basic early events of GFS wound healing have not been well described in humans, animal models have been used to delineate the initial stages of wound healing process. Despite a number of studies using animal models and human tissues, however, the early events of wound healing after GFS are still not clearly understood. In the context of general wound healing, observations in animal models and after GFS in humans suggest a sequence of events in GFS wound healing that occur in early bleb failure. Wound healing has been shown to involve an orderly series of events, including ECM degradation, cell migration, matrix synthesis, and tissue remodeling. After surgical trauma to the conjunctiva, episclera, and iris, blood vessels-constrict, and leakage of plasma proteins (including fibrinogen, fibronectin, and plasminogen) and blood cells occurs. Fibroblasts proliferate and migrate from the wound edges after GFS and-subsequently synthesize fibronectin, interstitial collagens, and glycosaminoglycans to form fibrovascular tissue, and later this tissue is remodeled to form a dense collagenous subconjuctival scar with scattered fibroblasts and blood vessels leading to wound scarring and filtration failure. In an animal model of conjunctival scarring, recombinant anti-TGF-beta2 treatment significantly improved glaucoma filtration surgery outcome compared to control (Cordeiro et al., Human Anti-Transforming Growth Factor-beta 2 Antibody: A New Glaucoma Anti-Scarring Agent, INVEST OPTHAMOL VIS SCI 1999; 40:2225–34). Mitomycin C and 5-fluorouracil are widely used as antiproliferative agents to inhibit fibroblast activation (Stamper et al., Hypotonous maculopathy after trabeculectomy with subconjunctival 5-fluorouracil, AM J OPHTHALMOL 1992;1 14:544–53; Parrish et al., "Late endophthalmitis"—filtering surgery time bomb? OPHTHALMOLOGY 1996; 103:1167–8; Greenfield, Bleb-related ocular infection. J GLAUCOMA 1998;7:132–6). A complication of the use of these agents is the production of thin, avascular blebs with an increased incidence of wound leak, hypotony and endophthalmitis. In addition, recent studies suggest that mitomycin C and 5-FU, in addition to their antiproliferative effects, induce fibroblast apoptosis (Crowston et al., Antimetabolite-induced apoptosis in Tenon's capsule fibroblasts, INVEST OPHTHALMOL VIS SCI 1998;39:449–54).

Early onset bleb leaks generally occur within a few months of surgery, and these leaks largely dependent on the technical aspects of the wound closure. In contrast, late-onset leaks are typically associated with thin, avascular blebs and generally occur months to years after the surgical procedure. In addition, a higher frequency of bleb-leaks is associated with mitomycin C treatment. Although mitomycin C is a widely used anti-proliferative agent, recent studies suggest that it leads to death of subconjuctival and scleral fibroblasts as well as vascular endothelial cells. This explains to some extent that mitomycin C may inhibit angiogenesis through a toxic effect on vascular endothelial cells and pleuripotent limbal stem cells, and may explain the high frequency of clinically avascular blebs seen after trabeculectomy with mitomycin C (Rubinfeld et al., Serious complications of topical mitomycin-C after pterygium-surgery, OPHTHALMOLOGY 1992;99:1647–54). The conjunctival wound healing in glaucoma filtration surgery is greatly influenced by the passage of aqueous through the surgical site. This is because of the presence of a number of cytokines, proinflammatory molecules, angiogenesis inhibitors, and plasminogen.

Late bleb leaks are more common in thin, avascular blebs, which occur more frequently with the use of adjunctive anti-metabolites (Greenfield et al., Late-onset bleb leaks after glaucoma filtering surgery, ARCH OPHTHALMOL 1998;1 16:443–7), or after full-thickness procedures (Le Guilloux, Glaucoma in the elderly, SOINS GERONTOL 1998:16–8). Recent studies suggest that a significant proportion of glaucoma filtering surgeries performed with anti-fibrosis agents such as mitomycin C, are associated with increased number of late-onset bleb leaks (Wilensky, Management of late bleb leaks following glaucoma filtering surgery, TRANS AM OPHTHALMOL SOC, 1992;90:161–8). The regulation of extracellular matrix (ECM) deposition is a key event in many physiological and pathological conditions. It is required for normal wound healing where synthesized ECM molecules replace mature connective tissue in remodeling. Excessive deposition or degradation of the remaining ECM, however, leads to pathological consequences. A tight balance between connective tissue synthesis and breakdown, is therefore, required for the normal functioning of all tissues. Matrix metalloproteinases ("MMPs"), in part, control this tissue balance. MMPs are a family of ECM degrading enzymes that share common functional domains and activation mechanism. To date, more than 20 members of the MMP family have been identified. MMPs are synthesized as secreted or transmembrane pro-enzymes and processed in the active form by the removal of an amino-terminal pro-peptide in the extracellular space and are capable of degrading all the components of the ECM including fibrillar and non-fibrillar collagens, fibronectin, laminin and basement membrane glycoproteins (Wojtowicz-Praga et al., Matrix Metalloproteinase Inhibitors, INVEST NEW DRUGS 1997; 15:61–75). The family of MMP enzymes includes, but is not limited to, collagenases, gelatinases, matrilysin and stromelyin; all of which have been shown to be involved in the degradation and remodeling of connective tissues.

As previously stated, the major determinant of glaucoma filtering surgery (GFS) success is the conjunctival wound healing response, with excessive post-operative scarring leading to filtration failure. Late bleb leaks may compromise the ability of the bleb to regulate IOP, and can lead to bleb-related complications such as infection and hypotony. Successful closure of late onset bleb leaks often requires surgical revision of the bleb.

GFS differs from most surgical procedures in that inhibition of wound healing is desirable to achieve surgical success. Successful filtration surgery is generally characterized by formation of a filtering bleb, which is a subconjunctival accumulation of aqueous. Histopathological examinations of functioning blebs demonstrate the appearance of loosely arranged connective tissue beneath the conjunctival epithelium. Early failed blebs demonstrate abnormally thickened, dense collagenous connective tissue beneath the conjunctival epithelium. In contrast, late failing blebs are often thin, and avascular.

Additional information regarding glaucoma filtering surgery is provided in R. Rand Allingham, "Filtering Surgery in the Management of Glaucoma," in Chandler and Grant's Glaucoma 4th Ed., Williams and Williams Eds., pp. 516–25 (1997), which is hereby incorporated by reference.

While surgical repair of leaking filtering blebs remains a treatment option, other improved and less invasive treatments for leaking filtering blebs, as well as treatment for ischemic damage of the retina and optic nerve would likely be widely accepted.

SUMMARY OF THE INVENTION

Leaks in the conjunctival filtering blebs may occur as either an early or late complication of glaucoma filtering surgery. These leaks decrease the ability of the glaucoma filtering surgery to regulate IOP and to control glaucoma symptoms.

Accordingly, in one aspect, the instant invention describes a method for the inhibition, prevention, and/or treatment of conjunctival bleb leaks.

Also provided is a method of inhibiting, preventing, and/or treating optical nerve damage in glaucoma patients.

More specifically, in one aspect, the present invention involves the use of pharmacologically effective, oral or topical, doses of a matrix metalloproteinase inhibitor to block excessive MMP activity in the blebs of patients who have undergone glaucoma filtering surgery. More specifically, the instant invention involves the use of tetracycline, or one of its analogues possessing MMP inhibitor activity, in patients who have undergone glaucoma filtering surgical treatment.

In another aspect, the present invention involves the use of a pharmacologically effective, topical, eye drop form of an MMP inhibitor to block unwanted MMP activity in retinas of patients who have ischemic damage to the retina and optic nerve. More particularly, the invention involves the use of tetracycline, or one of its analogues possessing MMP inhibitor activity, in patients who have ischemic damage to the retina and optic nerve.

The details of one or more embodiments of the invention are set forth in the accompanying description below. Although any methods and materials similar or equivalent to those described herein can be used in the practice or testing of the present invention, the preferred methods and materials are now described. Other features, objects, and advantages of the invention will be apparent from the description. In the specification and the appended claims, the singular forms also include the plural unless the context clearly dictates otherwise. Unless defined otherwise, all technical and scientific terms used herein have the same meaning as commonly understood by one of ordinary skill in the art to which this invention belongs. All patents and publications cited in this specification are incorporated herein by reference.

DETAILED DESCRIPTION OF THE DRAWINGS

The invention will be better understood by reference to the appended figures of which:

Figure 8:
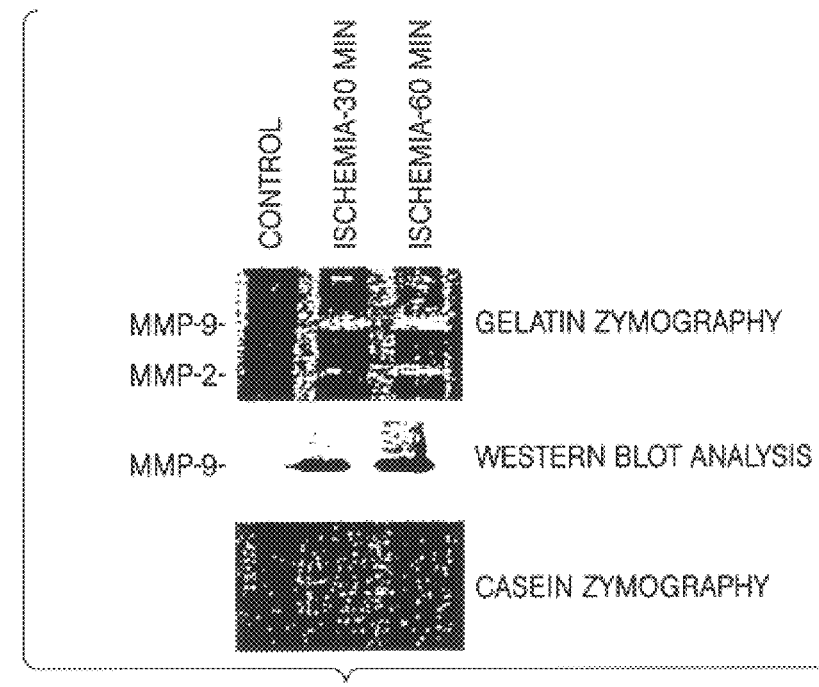
Figure 9:
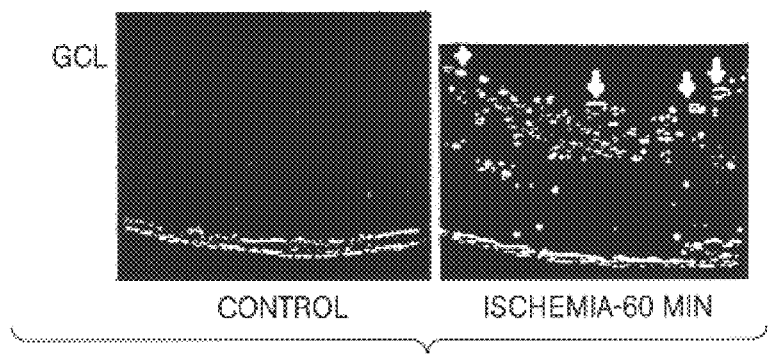
Figure 10:
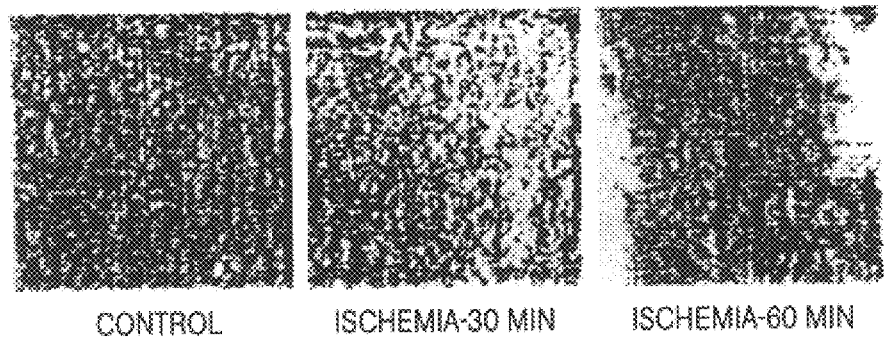
Figure 11:
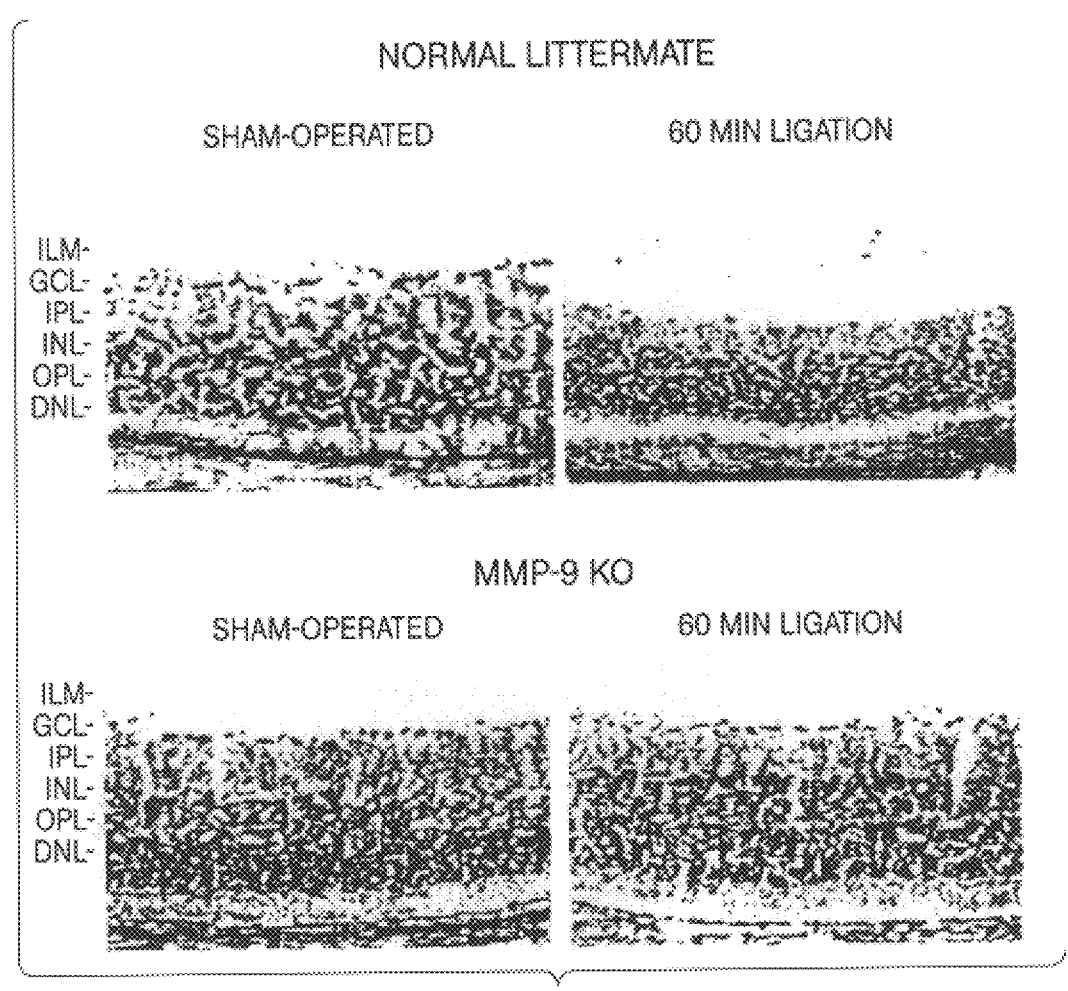

FIG. 8 shows a gelatin zymography, a western blot analysis and a casein zymography, which illustrate the detection of MMP activity in retinal extracts after 30 and 60 min ischemia and 2 days after reperfusion;

FIG. 9 illustrates the localization of MMP activity in retinas by in situ zymography. The arrows indicate the localization of gelatinolytic activity in the GC layer;

FIG. 10 illustrates β-gal reporter gene expression (MMP-9 promoter) in flat mount retinas from ischemic (30 min and 60 min) and control eyes; and FIG. 11 shows morphological analysis of retinal cross sections stained with H&E and which illustrate the inhibition of retinal degeneration in MMP-9 (gelB) knockout mice.

DETAILED DESCRIPTION OF THE INVENTION

Glaucoma filtration surgery is a common treatment used to lower IOP in glaucoma patients. Following glaucoma filtration surgery, the formation of holes in the conjunctival filtering blebs may occur as an early or late complication of the surgery. Holes may form as a result of the thinning of the conjunctival tissue. These holes in the conjunctival filtering blebs result in leakage of aqueous humor from conjunctival filtering blebs into the environment. If this leakage is left untreated, vision or eye-threatening complications may result. Although many treatment options have been proposed, successful closure of late bleb leaks following glaucoma filtering surgery remains a controversial and challenging medical problem.

As stated previously, early failed blebs following glaucoma filtering surgery demonstrate abnormally thickened, densely collagenous connective tissue beneath the conjunctival epithelium. Early onset bleb leaks generally occur within a few months of surgery, and these leaks largely depend on the technical aspects of the wound closure. In contrast, late failing blebs are typically associated with thin, avascular blebs and generally occur months to years after the surgical procedure. Although late onset leaking blebs are avascular, the majority of these late onset leaking blebs are surrounded by a vascular ring. It is believed that the avascularity of these blebs could be due to the presence of angiogenesis inhibitors in the bleb tissue. MMPs are known to cleave plasminogen, which is normally present in aqueous humor, to generate angiostatin, a potent inhibitor of angiogenesis.

It is believed that the formation of holes that lead to bleb leakage is due to excessive activity of enzymes belonging to the Matrix Metalloproteinase ("MMP") family. MMPs, a subclass of a much larger class of compounds known as proteases, are a family of secreted and membrane-bound zinc-endopeptidases that are capable of degrading all of the components of the extracellular matrix, including fibrillar and non-fibrillar collagens, fibronectin, laminin, and basement membrane glycoproteins. See Wojtowicz-Praga et al., INVEST. NEW DRUGS 15(1):61–75 (1997). The family of MMP enzymes includes, but is not limited to, collagenases, gelatinases, matrilysin and stromelysin; all of which have been shown to be involved in the degradation and remodeling of connective tissues.

MMP-9 (gelatinase B) is frequently expressed at sites of active tissue remodeling and neovascularization. Its excessive synthesis is generally associated with many pathological processes such as tumor invasion and corneal ulcers. It is further believed that ischemia induces MMP expression and the acute and increased protease activity is then associated with ganglion cell death in the retina. When late blebs leaks occur, they often happen in the avascular thin-walled filtering blebs, which are generally surrounded by the vascular ring. It is believed that these surrounding blood vessels produce and secrete MMPs into the avascular bleb tissue thus suggesting that chronic and increased protease activity, as well as the increased expression of MMP-9 in leaking filtering bleb tissue is associated with late-onset leakage of filtering blebs.

The inventors hypothesized that the presence of blood vessels surrounding the bleb might produce neutral proteases that may degrade the bleb tissue, perhaps in an effort to enter the bleb proper, and that these proteases might digest bleb tissue and cause bleb leaks. Bleb tissues and bleb leak fluids were obtained during bleb-revision surgery to determine whether late-onset bleb leaks were associated with increased protease activity. Zymography data indicated expression of MMP-9 in the leaking bleb tissues, but not in control tissues and normal aqueous humor. As expected, relatively similar levels of MMP-2 expression were observed in both in leaking bleb tissues as well as in aqueous humor from a normal individual and a tissue sample obtained from a patient with an overhanging bleb. Western blot analysis confirmed MMP-9 expression in leaking blebs The inventors have also determined that that expression of MMP-9 may lead to ECM degradation of conjuctival tissue and subsequently result in bleb leaks. MMP-9 expression, in addition to degrading the tissue, may also enzymatically cleave plasminogen to generate angiostatin, a potent angiogenic inhibitor. Although angiostatin is not commonly expressed in human vitreous it can accumulate in the leaking bleb tissue following cleavage of plasminogen leading to inhibition of angiogenesis, with resultant avascularity of the bleb. Indeed, our western blot analysis and immunolocalization data suggest expression of angiostatin in leaking-bleb tissues but not in control tissues. Angiogenesis requires invasion by endothelial cells and localized proteolytic modification of the ECM. MMPs are implicated in these processes owing to their ability to cleave ECM components. MMPs are expressed by and around forming blood vessels, and modification of MMP activity modulates endothelial cell proliferation or tubule formation. It is interesting to note that angiostatin, a proteolytic fragment of plasminogen, induces mitotic cell death of proliferating endothelial cells.

Tissue inhibitors of metalloproteinases (TIMPs) are naturally-occurring proteins that function by inhibiting matrix metalloproteinases. See id. TIMPs are able to maintain a balance between matrix destruction and formation. However, TIMPs are likely not suitable for pharmacological applications due to their short in vivo half-life. See id. Synthetic MMP inhibitors have been synthesized and have been shown to be more successful in inhibiting the function of the MMPs. Some MMP inhibitors have been implicated as anti-cancer agents that are capable of controlling tumor growth as well as inhibiting metastasis. See Brown, ADV. ENZYME REGUL. 35:293–301 (1995); Brown, PROC. ANN. MEET AM. ASSOC. CANCER RES. 37:633–44 (1996). Some examples of synthetic MMP inhibitors include batimastat, marimastat, bryostatins, tetracycline, and BB-3644. Tetracycline and many of its analogues have been demonstrated to be safe and effective broad spectrum MMP inhibitors.

In one aspect, the method of the instant invention is directed to the use of a pharmacologically effective amount of an MMP inhibitor, for example, tetracycline or an appropriate tetracycline analogue such as doxycycline which is active against MMPs. This would be done for patients who have undergone glaucoma filtering surgery, and will block MMP activity in the conjunctival filtering blebs. Thus, leakage from the conjunctival filtering blebs will be inhibited, prevented, and/or effectively treated. The present invention thus relates to a method of inhibiting, preventing, and/or treating late bleb leaks following glaucoma filtering surgery via the administration of a pharmacologically effective amount of an MMP inhibitor. More precisely, the invention involves the administration of a MMP inhibitor such as tetracycline, or one of the tetracycline analogues active against MMPs, either topically or orally, to a patient who has undergone glaucoma filtering surgery. As noted, tetracycline has the advantage of being already in widespread general use for a variety of other purposes, and it should thus be safe and relatively easy to apply in accordance with the method of the instant invention.

The method of the instant invention also relates to the use of a pharmacologically effective amount of MMP inhibitor, preferably tetracycline or an appropriate tetracycline analogue such as doxycycline, in patients affected with ischemic retinal damage or glaucoma (in which ischemia plays a major role in ganglion cell death). More specifically, the present invention relates to a method of inhibiting, preventing, and/or treating retinal damage via the administration of a pharmacologically effective amount of an MMP inhibitor. Another aspect of the present invention relates to the fact that, in addition to its MMP inhibitor effect, tetracycline is also a well-known antibiotic. The use of tetracycline in the method of the present invention thus affords an additional benefit, namely that the administration of tetracycline, either topically or orally, will also yield a beneficial antibiotic effect. This antibiotic effect could help prevent eye infections, both during the surgery and postoperatively. It is thus an added feature of this invention that the administration of tetracycline, or an appropriate tetracycline analogue, as described above, to a patient who has undergone glaucoma filtering surgery could inhibit, prevent, and/or treat bacterial infections as well as inhibit, prevent, and/or treat the occurrence of conjunctival bleb leaks following glaucoma filtering surgery. It is understood, however, that the invention is not limited to the administration of tetracycline and tetracycline analogues, and other MMP inhibitors may be used as well.

The present invention further relates to a method of inhibiting, preventing, and/or treating optic nerve damage. Data by the inventors shows that the action of MMP inhibitors in brain tissue may prevent nerve cell degeneration (Asahi et al., Role of Matrix Metalloproteinase 9 after Focal Cerebral Ischemia: Effects of Gene Knockout and Enzyme Inhibition with BB-94, J. CEREB BLOOD FLOW METAB; 2000, 20:1681–1689), as well as retinal neovascularization (Asahi et al., id), a leading cause of blindness in a variety of clinical conditions including diabetic retinopathy, retinopathy of prematurity, and retinal vein occlusions in which ischemia is a major factor. The process of neovascularization is tightly coupled to the production of MMPs in the retina. Therefore, in accordance with the method of the current invention, the application of MMP inhibitors to a patient who has undergone glaucoma surgery, or affected with diabetic retinopathy or retinal vein occlusions may be effective in the inhibition, prevention and/or treatment of retinal damage and optic nerve damage. The administration of MMP inhibitor may be either oral or topical and can be prophylactic or therapeutic. Because up-regulation and activation of MMPs is a final common pathway in the process of retinal ischemia and retinal neovascularization, pharmacological intervention of this process is an effective therapeutic approach to prevent retinal damage. As discussed above, optic nerve damage is one of the hallmarks of glaucoma. Therefore, in accordance with the method of the instant invention, the application or administration of MMP inhibitors to a patient who has undergone filtering surgery, may be effective in the inhibition, prevention, and/or treatment of optic nerve damage. More precisely, the administration of tetracycline, or an appropriate analogue thereof, to a patient who has undergone glaucoma filtering surgery may be useful in the inhibition, prevention, and/or treatment of optic nerve damage.

In the methods of the instant invention, administration is advantageously oral or topical. Moreover, administration can be prophylactic or therapeutic.

In animal testing, mice were treated with tetracycline in the range of 20–50 mg/kg i.p (intraperitonial) twice a day for the first day and 10–25 mg/kg for the subsequent 2–3 days.

In human testing, 1% doxycycline in the form of eye drops is applied on the eye four times a day and/or approximately 500 mg doxycycline are administered orally in the form of a pill, tablet, or capsule twice a day. These are the standard dosages which are well tolerated and in common usage. The invention is not, however, limited with respect to these dosages, and it is possible that dosages as much as ten times higher and/or lower than the standard dosages, and administered from between 1 and 4 times a day, may be even more effective for the present use.

The compositions administered in accordance with the methods of the present invention may be administered immediately after glaucoma filtration surgery and continued on a prophylactic basis for years. Advantageously, the compostions administered in accordance with the methods of the present invention may be administered at the first sign that blebs appear to be failing.

The invention is not however limited to oral and topical forms and formulations for other routes of administration are contemplated as well by the present invention. Examples of routes of administration include parenteral, e.g., intravenous, intradermal, subcutaneous, oral (e.g., inhalation), transdermal (i.e., topical), transmucosal, and rectal administration. Solutions or suspensions used for parenteral, intradermal, or subcutaneous application can include the following components: a sterile diluent such as water for injection, saline solution, fixed oils, polyethylene glycols, glycerine, propylene glycol or other synthetic solvents; antibacterial agents such as benzyl alcohol or methyl parabens; antioxidants such as ascorbic acid or sodium bisulfite; chelating agents such as ethylenediaminetetraacetic acid (EDTA); buffers such as acetates, citrates or phosphates, and agents for the adjustment of tonicity such as sodium chloride or dextrose. The pH can be adjusted with acids or bases, such as hydrochloric acid or sodium hydroxide. The parenteral preparation can be enclosed in ampoules, disposable syringes or multiple dose vials made of glass or plastic.

As used herein, "pharmaceutically acceptable carrier" is intended to include any and all solvents, dispersion media, coatings, antibacterial and antifungal agents, isotonic and absorption delaying agents, and the like, compatible with pharmaceutical administration. Suitable carriers are described in the most recent edition of Remington's Pharmaceutical Sciences, a standard reference text in the field, which is incorporated herein by reference. Preferred examples of such carriers or diluents include, but are not limited to, water, saline, Ringer's solutions, dextrose solution, and 5% human serum albumin. Liposomes, emulsions, and non-aqueous vehicles such as fixed oils may also be used. The use of such media and agents for pharmaceutically active substances is well known in the art. Except insofar as any conventional media or agent is incompatible with the active compound, use thereof in the compositions is contemplated. Supplementary active compounds can also be incorporated into the compositions.

A pharmaceutical composition of the invention is formulated to be compatible with its intended route of administration. Oral compositions generally include an inert diluent or an edible carrier. They can be enclosed in gelatin capsules or compressed into tablets. For the purpose of oral therapeutic administration, the active compound can be incorporated with excipients and used in the form of tablets, troches, or capsules. Oral compositions can also be prepared using a fluid carrier for use as a mouthwash, wherein the compound in the fluid carrier is applied orally and swished and expectorated or swallowed. Pharmaceutically compatible binding agents, and/or adjuvant materials can be included as part of the composition. The tablets, pills, capsules, troches and the like can contain any of the following ingredients, or compounds of a similar nature: a binder such as microcrystalline cellulose, gum tragacanth or gelatin; an excipient such as starch or lactose, a disintegrating agent such as alginic acid, Primogel, or corn starch; a lubricant such as magnesium stearate or Sterotes; a glidant such as colloidal silicon dioxide; a sweetening agent such as sucrose or saccharin; or a flavoring agent such as peppermint, methyl salicylate, or orange flavoring.

Pharmaceutical compositions for opthalmic topical administration may include opthalmic solutions, opthalmic sprays, ointments, perfusion and inserts. Opthalmic solutions in the form of eye drops generally consist of aqueous media. In order to accommodate wide ranges of drugs which have various degrees of polarity, buffers, organic carriers, inorganic carriers, emulsifiers, wetting agents, etc. can be added. Pharmaceutically acceptable buffers for opthalmic topical formulations include phosphate, borate, acetate and glucoronate buffers, amongst others. Drug carriers may include water, water mixture of lower alkanols, vegetable oils, polyalkylene glycols, petroleum based jelly, ethylcellulose, ethyl oleate, carboxymethylcellulose, polyvinylpyrrolidone, and isoproplyl myristrate. Opthalmic sprays generally produce the same results as eye drops and can be formulated in a similar manner. Some opthalmic drugs have poor penetrability across ocular barriers and are not administrable as drops or spray. Ointments may thus be used to prolong contact time and increase the amount of drug absorbed. Continuous and constant perfusion of the eye with drug solutions can be achieved by placing polyethylene tuping in the conjunctival sac. The flow rate of the perfusate is adjustable via a minipump system to produce continuous irrigation of the eye. Inserts are similar to soft contact lens positioned on the cornea, except that inserts are generally placed in the upper cul-de-sac or, less frequently, in the lower conjunctival sac rather than attached to the open cornea. Inserts are generally made of biologically soluble materials which dissolve in lacrimal fluid or disintegrate while releasing the drug.

Pharmaceutical compositions suitable for injectable use include sterile aqueous solutions (where water soluble) or dispersions and sterile powders for the extemporaneous preparation of sterile injectable solutions or dispersion. For intravenous administration, suitable carriers include physiological saline, bacteriostatic water, Cremophor EL (BASF, Parsippany, N.J.) or phosphate buffered saline (PBS). In all cases, the composition must be sterile and should be fluid to the extent that easy syringeability exists. It must be stable under the conditions of manufacture and storage and must be preserved against the contaminating action of microorganisms such as bacteria and fungi. The carrier can be a solvent or dispersion medium containing, for example, water, ethanol, polyol (for example, glycerol, propylene glycol, and liquid polyethylene glycol, and the like), and suitable mixtures thereof. The proper fluidity can be maintained, for example, by the use of a coating such as lecithin, by the maintenance of the required particle size in the case of dispersion and by the use of surfactants. Prevention of the action of microorganisms can be achieved by various antibacterial and antifungal agents, for example, parabens, chlorobutanol, phenol, ascorbic acid, thimerosal, and the like. In many cases, it will be preferable to include isotonic agents, for example, sugars, polyalcohols such as manitol, sorbitol, sodium chloride in the composition. Prolonged absorption of the injectable compositions can be brought about by including in the composition an agent which delays absorption, for example, aluminum monostearate and gelatin.

Sterile injectable solutions can be prepared by incorporating the active compound (e.g., a GPCR peptide or anti-GPCR-peptide antibody) in the required amount in an appropriate solvent with one or a combination of ingredients enumerated above, as required, followed by filtered sterilization. Generally, dispersions are prepared by incorporating the active compound into a sterile vehicle that contains a basic dispersion medium and the required other ingredients from those enumerated above. In the case of sterile powders for the preparation of sterile injectable solutions, methods of preparation are vacuum drying and freeze-drying that yields a powder of the active ingredient plus any additional desired ingredient from a previously sterile-filtered solution thereof.

In one embodiment, the active compounds are prepared with carriers that will protect the compound against rapid elimination from the body, such as a controlled release formulation, including implants and microencapsulated delivery systems. Biodegradable, biocompatible polymers can be used, such as ethylene vinyl acetate, polyanhydrides, polyglycolic acid, collagen, polyorthoesters, and polylactic acid. Methods for preparation of such formulations will be apparent to those skilled in the art. The materials can also be obtained commercially from Alza Corporation and Nova Pharmaceuticals, Inc. Liposomal suspensions (including liposomes targeted to infected cells with monoclonal antibodies to viral antigens) can also be used as pharmaceutically acceptable carriers. These can be prepared according to methods known to those skilled in the art, for example, as described in U.S. Pat. No. 4,522,811.

It is especially advantageous to formulate oral or topical compositions in dosage unit form for ease of administration and uniformity of dosage. Dosage unit form as used herein refers to physically discrete units suited as unitary dosages for the subject to be treated; each unit containing a predetermined quantity of active compound calculated to produce the desired therapeutic effect in association with the required pharmaceutical carrier. The specification for the dosage unit forms of the invention are dictated by and directly dependent on the unique characteristics of the active compound and the particular therapeutic effect to be achieved, and the limitations inherent in the art of compounding such an active compound for the treatment of individuals.

In addition to the MMP inhibitors described above, the invention also includes the use of pharmaceutical compositions and formulations comprising an MMP inhibitor in association with a pharmaceutically acceptable carrier, diluent, or excipient, such as for example, but not limited to, water, glucose, lactose, hydroxypropyl methylcellulose, as well as other pharmaceutically acceptable carriers, diluents or excipients generally known in the art.

The terms "pharmacologically effective amount", "pharmaceutically effective dosage" or "therapeutically effective amount" mean that amount of a drug or pharmaceutical agent that will elicit the biological or medical response of a tissue, system, animal or human that is being sought by a researcher or clinician.

Using a central retinal ligation model in mice, the inventors have found that retinal ischemia induces the synthesis of enzymes that degrade the tissue within the ischemia area. These enzymes have been determined to be MMPs. Although these enzymes are needed for normal functions, excessive amounts typically lead to disease and inappropriate expression of MMP activity constitutes part of the pathogenic mechanism associated with a wide range of diseases. These include breakdown and remodeling during invasive tumor growth and tumor angiogenesis (Westermark, J., Kahari, V-M. Regulation of matrix metalloproteinase expression in tumor invasion. FASEB J; 1999, 13: 781–792), and brain injury (Asahi et al., id). Their expression is known to increase in various inflammatory, malignant and degenerative diseases. Increased expression of MMPs is also implicated in ischemia-induced neuronal degeneration in the brain. Ischemia-induced expression of MMP-9 in the brain degrades ECM components such as laminin, fibronectin, and type IV collagen (Romanic A.M. et al., Matrix metalloproteinase expression increases after cerebral focal ischemia in rats. Inhibition of metelloproteinase-9 reduces infarct size. STROKE; 1998, 29: 1020–1030] and protease expression has been correlated with neuronal cell death (Chen Z. L., Strickland, S. CELL; 1997, 91: 917–925).

The retina is often considered the outermost portion of the brain and the ECM of retinal basal lamina of the ganglion cell inner limiting lining (ILM) in mouse and humans is comprised of mainly laminins, collagens IV and XVIII. The inventors have found ischemic damage to the mouse retina leads to MMP-9 production by cells in the ganglion cell layer, followed by degradation of ECM composing of retinal ILM and then ganglion cell death by apoptosis. In addition, by creating a similar type of retinal injury, the inventors have found that ganglion cell death is prevented in a genetically engineered mouse strain in which the MMP-9 gene is deleted (MMP-9 knockout mice).

It is believed that the degradation of the ECM components in the ILM may affect the survival of ganglion cells due to alterations in cell-matrix interactions. The altered-cell matrix interactions may then cause activation of caspases, leading to apoptosis of ganglion cells as seen in ischemic conditions to the retina. At the present time, the mechanisms that lead to ganglion cell death during retinal ischemias are not well understood. The proteases that are expressed in response to ischemia invariably degrade the ECM in the affected area and cause irreversible vision loss. The method of the present invention offers a new way to prevent retinal ganglion cell death and subsequent optic nerve damage.

In accordance with the present invention, the available clinical history of the patients from whom tissue specimens were obtained is provided in Table 1:

TABLE 1

Clinical Findings in Surgical Specimens

| Patient Age (years/sex) | Tissue | Antimetabolite Treatment | IOP (mmHg) | Analyses |
|---|---|---|---|---|
| 74 Y/M | Bleb | Yes | OS18 | G/C, IZ |
| 73 Y/M | Bleb | Yes | OS1 | G/C |
| 73 Y/M | Aqueous |  | OS1 | G/C |
| 64 Y/F | Bleb | No | OD14 | I, W |
| 63 Y/M | Overhanging Bleb | No | OS14 | I, W, IZ |
| 55 Y/F | Overhanging Bleb | No | OD6 | G/C |
| 77 Y/M | Bleb |  | OD1 | I, IZ |
| 71 Y/M | Tenon's fascia | No | 20 | G/C |
| 76 Y/F | Bleb |  | 37 | G/C, W, I |
| 70 Y/M | Bleb | No | OD2 | G/C |
| 65 Y/F | Bleb | No | OD5 | G/C |

Figure 1A:
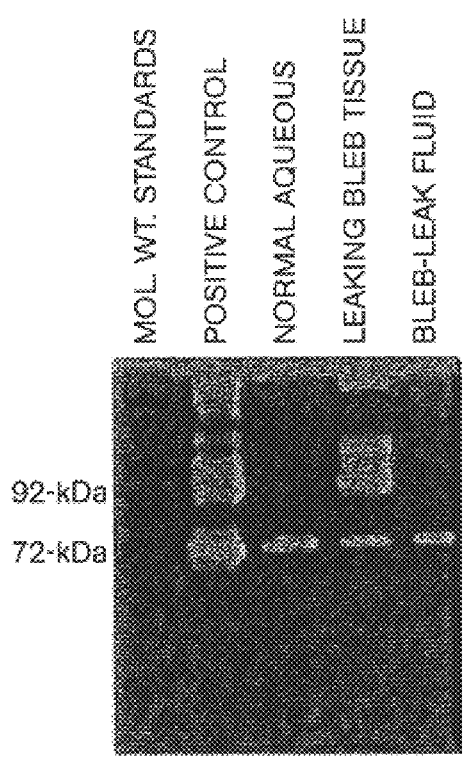
FIG. 1A illustrates a gelatin zymography of extracts from leaking bleb tissue, bleb leak fluid and aqueous humor in which the position of gelatinase A (72-kDa) and B (92-kDa) is indicated.
Figure 1B:
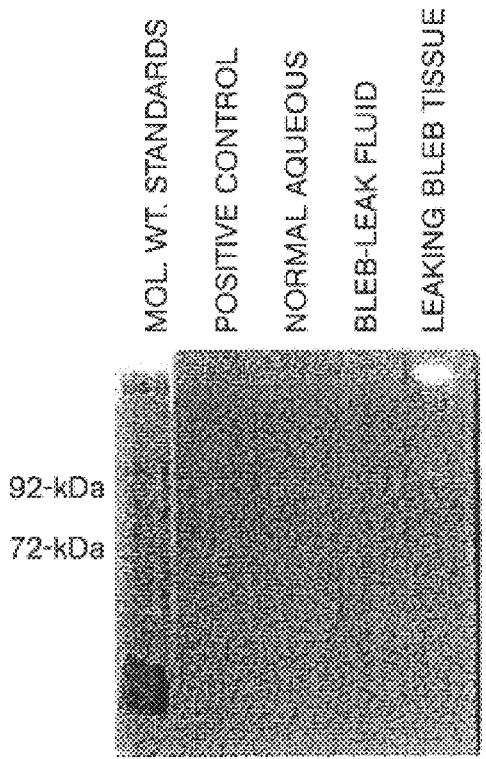
FIG. 1B illustrates a casein zymography of extracts from leaking bleb tissue, bleb leak fluid and aqueous humor.
Figure 2:
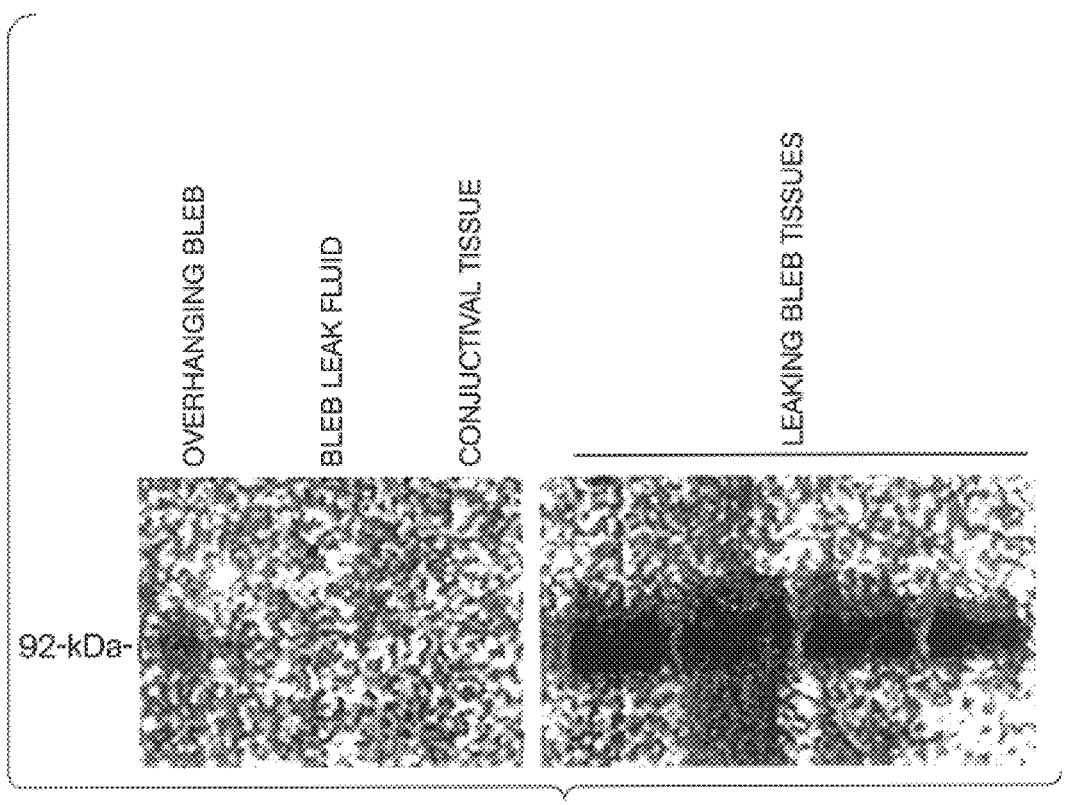
FIG. 2 is a western blot illustrating the identity of the 92 kDa protease present in the leaking bleb tissues as gelatinase B.
Figure 3:
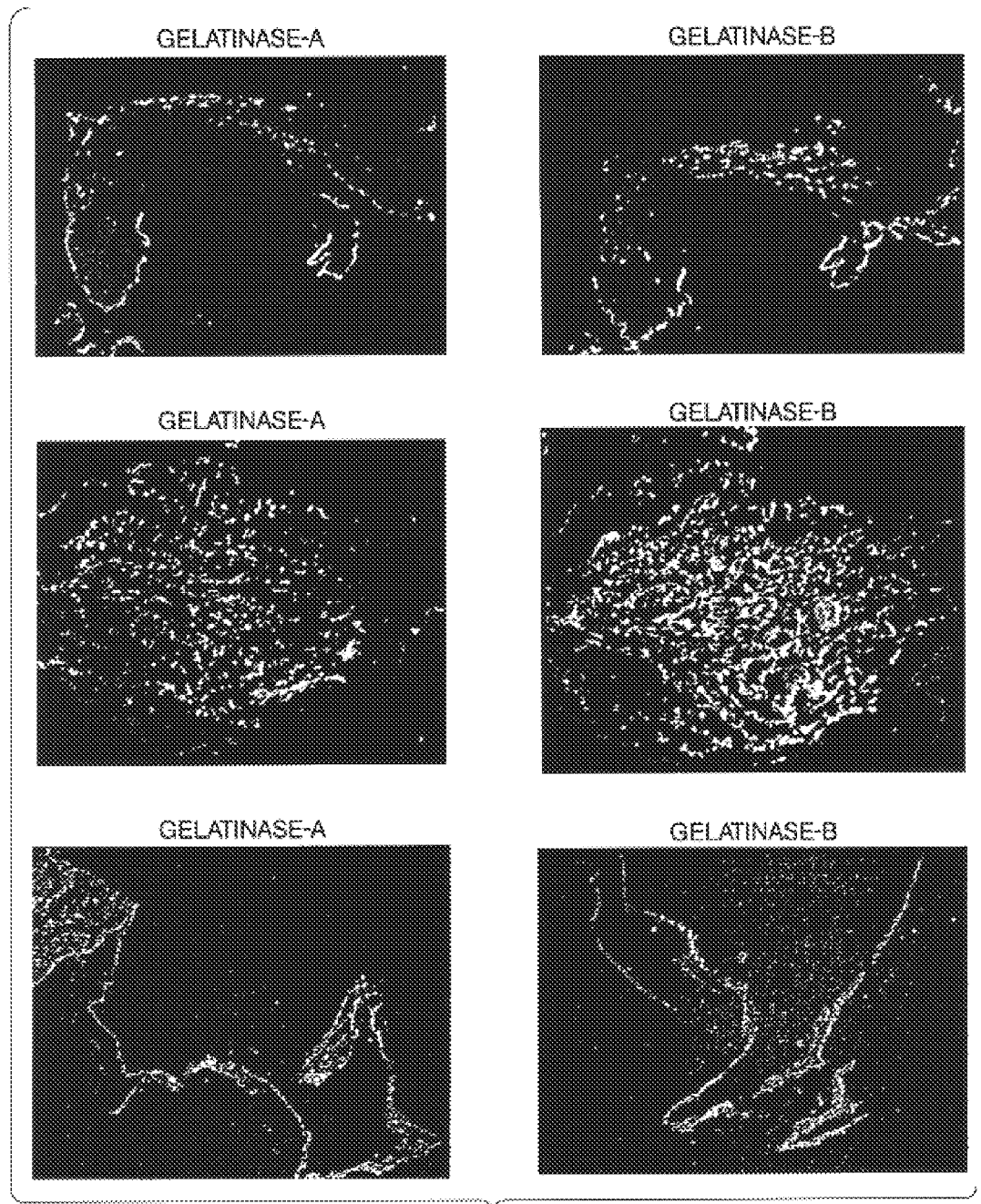
FIG. 3 illustrates positive gelatinase A and B immunostaining of frozen tissue sections from two leaking bleb specimens.
Figure 4:
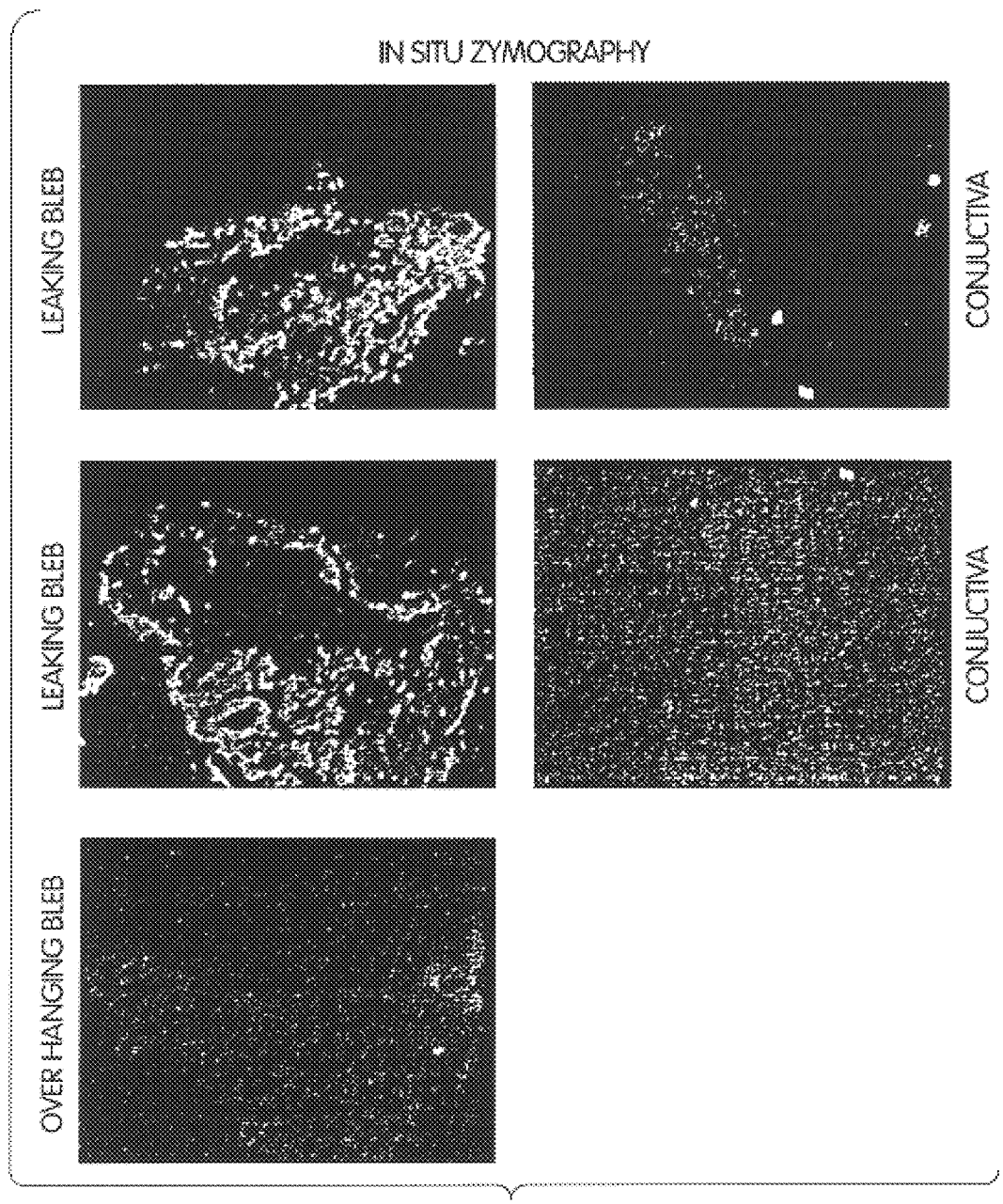
FIG. 4 illustrates the tissue localization of gelatinolytic activity in in situ zymography performed on frozen tissue sections.

G/C = gelatin/casein zymography; I = immunohistochemistry; W = western blot analysis; IZ = In situ zymography To analyze for the presence of neutral proteinases, tissue proteins were extracted and run on gelatin and casein substrate gels (zymography). Representative results are shown in FIGS. 1A and 1B. A 65-kDa protease of a size appropriate to be the proenzyme from gelatinase A was consistently present in specimens derived from leaking blebs and bleb-leak fluid, and also in aqueous humor obtained from normal individuals (FIG. 1A). In contrast, a 92-kDa gelatinase, of a size appropriate to be the proenzyme of gelatinase B was found in specimens derived from leaking bleb tissue. A small amount of this protease was also seen in bleb leak fluid but not in aqueous humor donated from normal individuals. Casein zymography indicated the presence of a high molecular weight caseinolytic activity in the leaking bleb tissue but not in bleb leak fluid or in normal aqueous humor (FIG. 1B). Western blot analysis confirmed the identity of the 92-kDa protease present in the leaking bleb tissues as gelatinase B (FIG. 2) and demonstrated that absence of the enzyme in overhanging bleb tissue. Positive immunostaining of frozen tissue sections from two leaking bleb specimens was observed positive for both gelatinase A and B (FIG. 3). In contrast, strong immunostaining for gelatinase B was observed in leaking bleb tissues compared to love levels of gelatinase A. In addition, gelatinase B was totally absent in overhanging bleb tissue; low levels of gelatinase A were present in this tissue as expected. Zymography and western blot analysis assay the presence of specific proteases, but do not provide an assessment of protease activity. To determine the tissue localization of gelatinolytic activity, in situ zymography was performed on frozen tissue sections. FIG. 4 indicates that the leaking bleb tissue had gelatinolytic activity localized in the tissues, whereas the conjunctival tissue and an overhanging bleb were negative.

Figure 5:
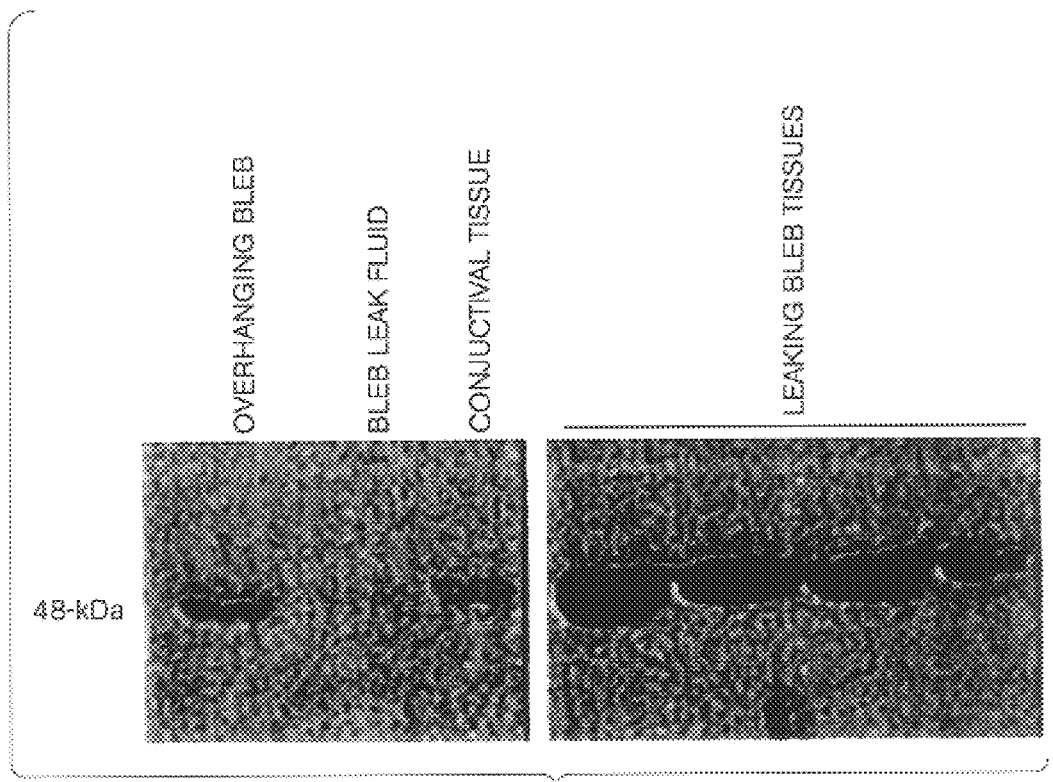
FIG. 5 illustrates a western blot showing the avascularity of the leaking blebs associated with the presence of angiostatin.
Figure 6:
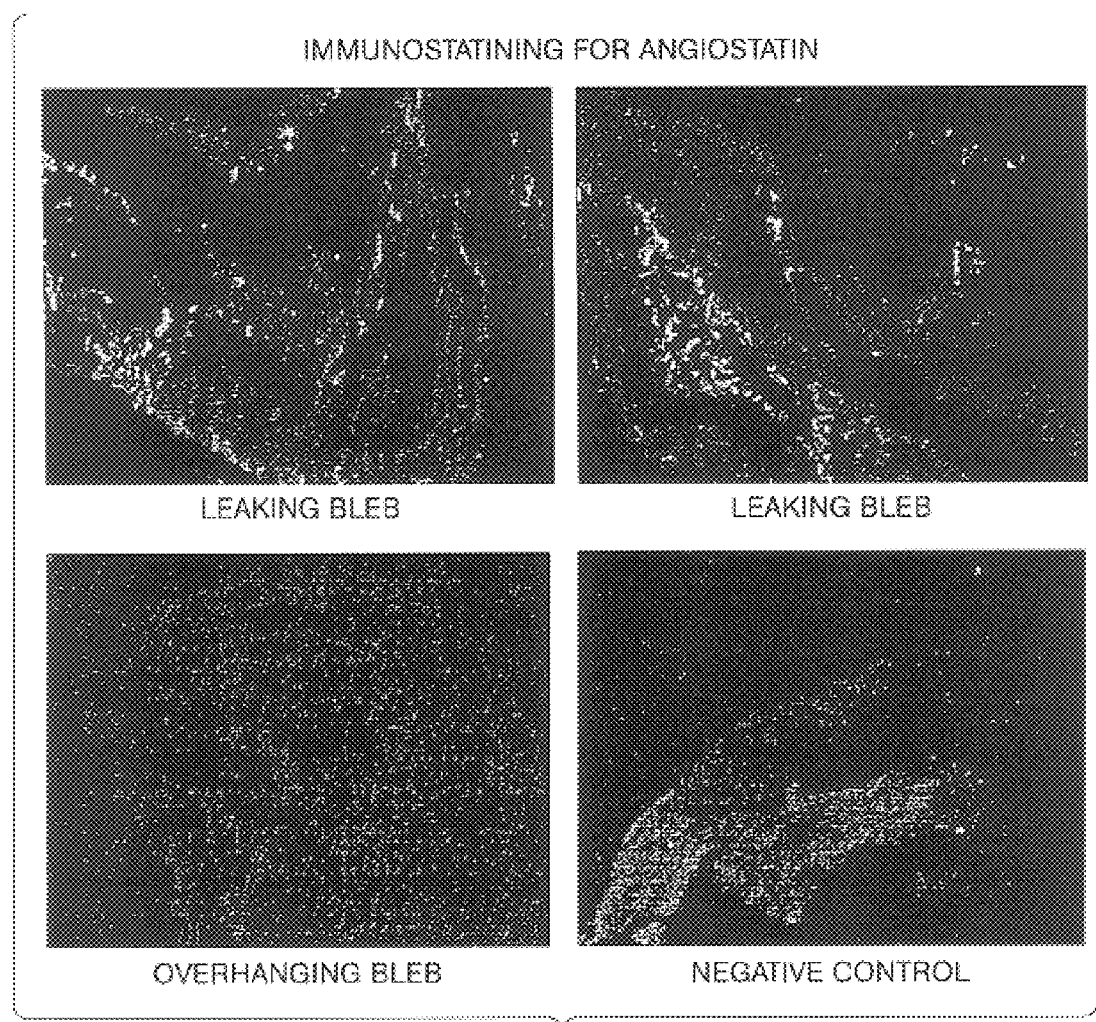
FIG. 6 illustrates the results of immunostaining studies that indicate increased expression of angiostatin in leaking bleb tissue but not in overhanging bleb tissue.

The majority of late onset leaking blebs are avascular but surrounded by a vascular ring. The inventors hypothesized that the avascularity of these blebs was due to the presence of angiogenesis inhibitors in the bleb tissue. As previously recited, MMPs are known to cleave plasminogen, which is normally present in aqueous humor, to generate angiostatin, a potent inhibitor of angiogenesis. To determine whether the avascularity of the leaking blebs is associated with the presence of angiostatin, western blot analysis was performed on leaking bleb tissues and bleb leak fluid. FIG. 5 indicates that a low level of angiostatin is present in the overhanging bleb tissue and conjunctival tissues examined. In contrast, an increased amount of angiostatin was observed in all the leaking bleb tissues. Angiostatin was not found in bleb leak fluid. To determine the tissue localization of angiostatin, immunolocalization studies were performed on frozen cross sections using angiostatin antibody. Consistent with the aforementioned western blot data, immunolocalization studies also indicate increased expression of angiostatin in the leaking bleb tissue but not in an overhanging bleb tissue (FIG. 6).

While surgical repair of leaking filtering blebs remains a treatment option for leak repair, inhibition of MMP activity appears to decrease the likelihood or lead to the resolution of late-bleb leaks.

The invention is further defined by reference to the following examples describing the experimental protocol with regard to elucidating the role of MMPs in conjunctival bleb tissue, the role of MMPs in retinal damage and optic nerve damage, as well as the preparation of the composition and dosage forms of the MMP inhibitors of the present invention. It will be apparent to those skilled in the art that many modifications, both to the materials and methods, may be practiced without departing from the purpose and interest of the invention.

EXAMPLES

A. Using MMP Inhibitors in the Treatment of Leaking Blebs Following Glaucoma Filtering Surgery Methods: Leaking bleb tissues and adjacent conjunctival tissues were collected along with bleb fluid and aqueous humor from patients undergoing bleb revision surgeries. Proteins from tissue samples were extracted and proteases were detected by gelatin and casein substrate zymography. Western blot analysis was performed detected MMP-9 and angiostatin. Immunolocalization studies were performed on frozen sections from bleb leak tissues and control conjunctival tissues to detect MMP-2, MMP-9 and angiostatin.

Preparation of tissue extracts: Bleb tissue was collected during bleb revision surgery and quickly transferred to laboratory by keeping them on ice. Tissue was obtained from patients during bleb revision surgery with the written consent of the patients. A portion of the bleb tissue was placed in a 1.5 ml eppendorf tube containing 40 ul RIPA buffer (1% nonidet P40, 20 mM Tris-HCl, 150 mM NaCl, 1 mM $Na_3VO_4$, 5 mM EDTA, 0.1 mg/ml aprotinin, 1 mM PMSF, pH 7.4) on ice. Tissues were homogenized with a Teflon homogenizer and centrifuged at 10,000 rpm for 5 min at 4° C. The supernatants were collected and total protein concentration in each sample was determined using the Bradford assay (Bio-Rad laboratories, Hercules, Calif.).

Gelatin/casein zymography: Zymography analysis was performed to detect gelatinases. Aliquots containing 20 ug total protein were mixed with 4× gel-loading buffer and separated at 4 C on 10–12% SDS gel containing 2% gelatin or casein. The gels were washed twice (30 min each) with rinse buffer (2.5% Triton X-100, 50 mM Tris-HCl, pH 7.5). After washes with Triton X-100, each gel was incubated in activation buffer (50 mM Tris-HCl, pH 7.5, and 5 mM $CaCl_2$), for 16–18 h at 37° C., to allow proteinases to degrade gelatin/casein in their immediate vicinity. After rinsing with water, each gel was stained with Coomassie blue for 1–2 h.

Incubation of the gel with destaining solution (acetic acid: methanol: water [1:3:6]) revealed gelatinases as clear bands against a dark background. The identity of MMPs was based on their molecular weight, comparing to standard molecular weight markers and purified proteinases.

Immunohistochemistry: Immunohistochemistry of bleb tissues was performed according to standard protocols. The bleb tissue was embedded in OCT compound (Miles, Elkhart, Ind.) and quickly frozen in liquid nitrogen; traverse, 8-um thick sections were cut with a Leica cryostat and placed onto superfrost plus slides (Fisher Scientific, Pittsburgh, Pa.). These sections were stored at −20° C. until use. For use, slides were returned to room temperature, the tissue was fixed by incubating them in 4% paraformaldehyde at room temperature, washed with PBS (137 mM NaCl, 2.68 mM KCl, 10 mM $Na_2HPO_4$, and 1.76 mM $KH_2PO_4$, pH 7.4). Primary antibodies against human MMP-9, MMP-2, angiostatin were diluted in PBS containing 2% goat serum and incubated for 2 h at room temperature or overnight at 4° C. Sections were then washed with PBS, and incubated in appropriate fluorescently labeled secondary antibodies diluted in PBS for 1 h at room temperature. After washes in PBS, sections were mounted with a solution containing 90% glycerol and 10% water.

In situ zymography: Frozen sections were incubated with FITC-labeled DQ-gelatin, (Molecular Probes, Eugene, OR) which is not fluorescent under normal conditions. However, the digestion of this substrate by proteases present in the tissue yields cleaved FITC-peptides, which will enable us to locate the gelatinolytic activity. For in situ zymography, frozen retinal cross sections were incubated with reaction buffer (0.05M Trs-HCl, 0.15M NaCl, 5 mM $CaCl_2$, and 0.2 mM $NaN_3$, pH 7.6) containing 40 ug/ml DQ-gelatin overnight. At the end of the incubation period and without fixation or washing, gelatinolytic activity of MMPs was localized and photographed by fluorescence microscopy (Nikon E400).

Western blot analysis: To investigate the protein expression patterns in control and leaking bleb tissues, equal amounts (20 ug) of total proteins were mixed with 4× sample buffer (252 mM Tris-HCl, 40% glycerol, 4% SDS, 0.01% bromophenol blue). Each sample was separated 10–12% SDS-PAGE gels and transferred to nylon membranes. The membranes were blocked with 10% non-fat dry milk in PBS containing 0.1% Tween-20 (PBS-T). Antibodies against MMP-9 (obtained from Dr. Robert Senior, Washington University) and MMP-2 (Sigma, St. Louis, Mo.) were used to detect the proteins on the membranes. A monoclonal antibody against human plasminogen that cross-reacts with the kringle 1–3 region of angiostatin (Enzyme Research Laboratories, Inc. South Bend, Ind.) was used to detect angiostatin expression in the extracts. After washing with PBS-T, the membrane was incubated with peroxidase-conjugated secondary antibody at room temperature for 1 hr. Finally the proteins were detected using Chemical luminescence Kit (ECL, Amersham Pharmacia Biotech, Piscataway, N.J.). Purified human MMP-9 and human MMP-2 (from Chemicon) were used as standards.

Figure 7:
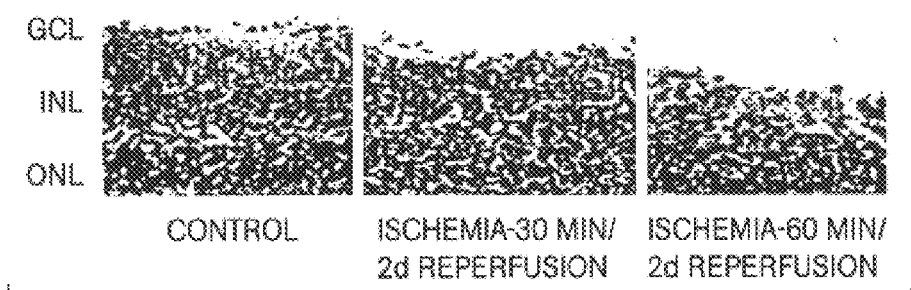
FIG. 7 illustrates the morphological analysis of retinal cross sections stained with H&E.

B. Using MMP Inhibitors to Prevent Retinal Degeneration and Optical Nerve Damage Central retinal artery ligation causes retinal ischemia and loss of ganglion cells: Adult CD-1 mice were anesthetized and retinal ischemia was created by placing a nylon suture around the optic nerve sheath and tightened sufficiently to inhibit retinal blood flow. After 30 and 60 min ischemia, eyes were re-perfused by removing the suture. Eyes (n=6) enucleated 2 days after re-perfusion were embedded in OCT compound and cut into 8 um frozen cross sections. Data in FIG. 7 indicates that 30 and 60 min retinal ischemia is sufficient to cause 25–30% retinal ganglion cell (RGC) loss within 2 days of post injury, compared to contralateral control retinas. Unless indicated, the results presented were obtained from control and ischemic retinas after 30 and 60 min ischemia, and 2 days of re-perfusion.

MMP-9 is induced in ischemia injured but not in control retinas: Total retinal proteins were extracted from control and ischemic retinas 2 days post ischemia, and MMP activity was analyzed by gelatin/casein substrate-zymography by loading equal amount of protein (20 ug) from each treatment. Our results indicate that MMP-9 was the predominant protease induced by retinal ischemia (FIG. 8, top panel). MMP activity was not detected in control mice. No caseinolytic activity was detected in either ischemic or control retinas (FIG. 8, bottom panel). Western blot analysis indicated increased expression of MMP-9 protein in ischemic retinas (FIG. 8, middle panel), consistent with the zymography data.

Protease activity is localized in retinal ganglion cell layer: Cellular source of gelatinolytic activity in frozen retinal sections was determined by in situ zymography. Unlike regular zymography, which detect only the net proteolytic activity from extracted cells/tissues and conditioned medium, this new technique (Oh et al., 1999) will enable us to locate the sites/origin of net gelatinolytic activity in a given tissue. This technique utilizes FITC-labeled DQ-Gelatin (Molecular Probes, OR) (non-fluorescent under normal conditions), which when digested by proteases yields cleaved gelatin-FITC peptides that are fluorescent thus enabling us to localize the gelatinolytic activity in the tissue. When frozen retinal sections from ischemic and non-ischemic eyes were incubated with DQ-gelatin, gelatinolytic activity was localized in the retinal ganglion cell layer of the ischemic but not in control retinas (FIG. 9), indicating the induction of gelatinolytic activity in the RGC layer.

MMP-9 transcriptional promoter is constitutively active in retinal ganglion cells of MMP-9 transgenic mice: In order to test the hypothesis that MMP-9 expression is induced in the retinal ganglion layer, a mouse model system was used in which both MMP-9 promoter activity and RGC loss can be simultaneously tested. We used MMP-9/lacZ transgenic mouse line3445, in which DNA sequences between −522 and +19 of the rabbit gelatinase B (MMP-9) gene constitute a minimal promoter that drives the appropriate developmental and injury-induced reporter gene (lacZ, [beta-galactosidase]) expression (Mohan et al., 1998), including constitutive promoter activity in ganglion cell layer. The inventors hypothesized that ischemic conditions that leads to MMP-9 protein expression in the retina also leads to increased MMP-promoter activity in ganglion cell layer. Moreover, this is where the gelatinolytic activity is localized in the ganglion cell layer (FIG. 10). To test this hypothesis, retinal ischemia was created in MMP-9/lacZ transgenic mice for 30 min and 60 min and 2 days of re-perfusion retinas were carefully dissected and MMP-9 promoter activity was determined in flat mount retinas by β-gal staining. The data in FIG. 10 indicate constitutive MMP-9 promoter activity, seen as dot-like staining pattern, in retinal ganglion cells of control mice. In contrast, the intensity of MMP-9 promoter activity was induced in ischemic retinas after 30 min and 60 min ischemia. These results suggest that ischemia induces MMP-9 promoter activity (indirectly by β-gal reporter gene expression) in cells of the retinal ganglion cell layer.

Inhibition of ganglion cell loss in MMP-9 knockout mice: Because MMP-9 is correlated with ganglion cell loss, we used MMP-9 knockout mice to determine whether ganglion cell loss is prevented in these mice. MMP-9 KO mice and normal littermates were anesthetized and retinal ischemia was created as described above. After 60 min ischemia, eyes were re-perfused for two days. Enucleated eyes were embedded in OCT compound and cut into 8 um frozen cross sections. Data in FIG. 11 (upper panel) indicates that 60 min retinal ischemia is sufficient to cause 25–30% retinal ganglion cell (RGC) loss in normal littermates, compared to contralateral control retinas. Interestingly, no ganglion cell loss was observed in MMP-9 KO mice (FIG. 11, lower panel), compared to contralateral control eyes and normal littermates showing that MMP-9 is a key component in ischemia-induced retinal ganglion cell loss.

OTHER EMBODIMENTS

It is to be understood that while the invention has been described in conjunction with the detailed description thereof, the foregoing description is intended to illustrate and not limit the scope of the invention, which is defined by the scope of the appended claims.

It is also to be understood that the drawings are not necessarily drawn to scale, but that they are merely conceptual in nature.

We claim:

1. A method of treating or preventing leakage of a conjunctival bleb in the eye of a subject who has undergone glaucoma filtering surgery which comprises the steps of:
   a. preparing a dosage comprising a pharmaceutically effective amount of a matrix metalloproteinase inhibitor;
   b. administering the dosage to a subject in need thereof following glaucoma filtering surgery.

2. The method as recited in claim 1, wherein the pharmaceutically effective dosage is administered orally.

3. The method as recited in claim 1, wherein the pharmaceutically effective dosage is topically administered to the eye of said subject.

4. The method as recited in claim 1, wherein the matrix metalloproteinase inhibitor is a protease inhibitor.

5. The method as recited in claim 4, wherein the protease inhibitor is tetracycline or an analog thereof.

6. The method as recited in claim 4, wherein the protease inhibitor is doxycycline.

7. The method as recited in claim 1, wherein the matrix metalloproteinase inhibitor is tetracycline.

8. The method as recited in claim 1, wherein the matrix metalloproteinase inhibitor is doxycycline.

9. The method as recited in claim 2, wherein the pharmaceutically effective dosage consists of approximately 500 mg doxycycline in the form of a pill for ingestion by mouth.

10. The method as recited in claim 3, wherein the pharmaceutically effective dosage consists of 1% doxycycline administered to the eye of said subject.

11. A method of treating or preventing leakage of a conjunctival bleb in a subject who has undergone glaucoma filtering surgery, the method comprising the administration of a pharmaceutically effective dosage of tetracycline or a tetracyline analog to a subject in need thereof.

12. The method as recited in claim 1, wherein the pharmaceutically effective dosage is administered orally.

13. The method as recited in claim 9, wherein the pharmaceutically effective dosage is topically administered to the eye of said subject.

14. The method as recited in claim 12, wherein the pharmaceutically effective dosage consists of approximately 500 mg doxycycline in the form of a pill for ingestion by mouth.

15. The method as recited in claim 13, wherein the pharmaceutically effective dosage consists of 1% doxycycline administered to the eye of said subject.

16. A method of treating or preventing optic nerve damage in a subject, which comprises the steps of:
    a. preparing a dosage comprising a pharmaceutically effective amount of a matrix metalloproteinase inhibitor;
    b. administering the dosage to a subject in need thereof following glaucoma filtering surgery.

17. The method as recited in claim 16, wherein the pharmaceutically effective dosage is administered orally.

18. The method as recited in claim 16, wherein the pharmaceutically effective dosage is topically administered to the eye of said subject.

19. The method as recited in claim 16, wherein the matrix metalloproteinase inhibitor is a protease inhibitor.

20. The method as recited in claim 19, wherein the protease inhibitor is tetracycline or an analog thereof.

21. The method as recited in claim 19, wherein the protease inhibitor is doxycycline.

22. The method as recited in claim 16, wherein the matrix metalloproteinase inhibitor is tetracycline or an analog thereof.

23. The method as recited in claim 16, wherein the matrix metalloproteinase inhibitor is doxycycline.

24. The method as recited in claim 17, wherein the pharmaceutically effective dosage consists of approximately 500 mg doxycycline in the form of a pill for ingestion by mouth.

25. The method as recited in claim 18, wherein the pharmaceutically effective dosage consists of 1% doxycycline administered to the eye of said subject.

26. The method as recited in claim 16, wherein said subject is human.

27. A method for the treatment or prevention of conjunctival bleb leakage in a subject following glaucoma filtering surgery, comprising administering a dosage form comprising a therapeutically effective amount of a matrix metalloproteinase inhibitor in association with a pharmaceutically acceptable carrier, excipient, diluent or adjuvant.

28. The method as recited in claim 27, wherein the dosage form is adapted for oral or topical administration.

29. The method as recited in claim 27, wherein said subject is human.

30. The method as recited in claim 27, wherein the therapeutically effective amount consists of 1% doxycycline administered to the eye of said subject.

31. The method as recited in claim 30, wherein said 1% doxycycline is administered to an eye of said subject four times a day.

32. The method as recited in claim 27, wherein the therapeutically effective amount consists of approximately 500 mg doxycycline in the form of a pill for ingestion by mouth.

33. A method for treating ischemic damage to the retina and optic nerve, the method comprising the steps of:
    a. preparing a dosage comprising a pharmaceutically effective amount of a matrix metalloproteinase inhibitor;
    b. administering the dosage to a subject in need thereof.

34. The method as recited in claim 33, wherein the pharmaceutically effective dosage is administered orally.

35. The method as recited in claim 33, wherein the pharmaceutically effective dosage is topically administered to the eye of said subject.

36. The method as recited in claim 33, wherein the matrix metalloproteinase inhibitor is a protease inhibitor.

37. The method as recited in claim 36, wherein the protease inhibitor is tetracycline or an analog thereof.

38. The method as recited in claim 36, wherein the protease inhibitor is doxycycline.

39. The method as recited in claim 33, wherein the matrix metalloproteinase inhibitor is tetracycline.

40. The method as recited in claim 33, wherein the matrix metalloproteinase inhibitor is doxycycline.

41. The method as recited in claim 34, wherein the pharmaceutically effective dosage consists of approximately 500 mg doxycycline in the form of a pill for ingestion by mouth.

42. The method as recited in claim 34, wherein the pharmaceutically effective dosage consists of 1% doxycycline administered to the eye of said subject.

* * * * *